(12) United States Patent
Wolleschensky et al.

(10) Patent No.: US 7,999,238 B2
(45) Date of Patent: Aug. 16, 2011

(54) ARRANGEMENT FOR PROCESSING SIGNALS AT THE OUTPUT OF A MULTICHANNEL DETECTOR

(75) Inventors: Ralf Wolleschensky, Jena (DE); Mirko Liedtke, Jena (DE)

(73) Assignee: Carl Zeiss MicroImaging GmbH, Jena (DE)

( * ) Notice: Subject to any disclaimer, the term of this patent is extended or adjusted under 35 U.S.C. 154(b) by 150 days.

(21) Appl. No.: 12/375,389

(22) PCT Filed: Jul. 16, 2007

(86) PCT No.: PCT/EP2007/006279
§ 371 (c)(1),
(2), (4) Date: Apr. 13, 2009

(87) PCT Pub. No.: WO2008/011999
PCT Pub. Date: Jan. 31, 2008

(65) Prior Publication Data
US 2009/0250627 A1  Oct. 8, 2009

(30) Foreign Application Priority Data
Jul. 28, 2006 (DE) .......................... 10 2006 034 905

(51) Int. Cl.
*G01N 21/64* (2006.01)
(52) U.S. Cl. .................................... 250/458.1
(58) Field of Classification Search .................. 250/216, 250/458.1; 356/317; 359/368
See application file for complete search history.

(56) References Cited

U.S. PATENT DOCUMENTS

| 6,529,271 B1 | 3/2003 | Engelhardt |
| 7,456,026 B2 | 11/2008 | Janka et al. |
| 2004/0032651 A1 | 2/2004 | Storz et al. |
| 2004/0120455 A1* | 6/2004 | Luryi et al. ..................... 378/44 |
| 2005/0213188 A1 | 9/2005 | DeSimone et al. |

FOREIGN PATENT DOCUMENTS

| DE | 198 58 456 | 7/2000 |
| DE | 100 08 594 | 8/2001 |
| DE | 100 33 180 | 5/2002 |
| DE | 102 31 776 | 1/2004 |
| DE | 10 2005 049 723 | 4/2007 |

OTHER PUBLICATIONS

XP-002290909 invited paper "Sensitive imaging of spectrally overlapping fluorochromes using the LSM 510 META" Dickinson, et al., Proceedings of SPIE, vol. 4620 (2002), pp. 123-136.
XP-010744863 CThNN5 "Single-shot fluorescence lifetime imaging using a novel segmented gated optical intensifier" Elson, et al.., IEEE, vol. 2, May 20, 2004, pp. 751-752.
XP-002433694 "High-speed scanning confocal microscope for the life sciences" Wolleschensky, et al., Proceedings of the SPIE, vol. 5860, No. 1, 2005, pp. 87-94.

\* cited by examiner

*Primary Examiner* — David P Porta
*Assistant Examiner* — Marcus H Taningco
(74) *Attorney, Agent, or Firm* — Frommer Lawrence & Haug LLP

(57) ABSTRACT

An arrangement for signal processing at the output of a multichannel detector in the spectrally resolved acquisition of time-variable fluorescence phenomena in a microscope, particularly lifetime measurements, is characterized in that an FPGA (free programmable gate array) is arranged downstream of the output of the multichannel detector.

5 Claims, 5 Drawing Sheets

ARRANGEMENT FOR PROCESSING SIGNALS AT THE OUTPUT OF A MULTICHANNEL DETECTOR

The present application claims priority from PCT Patent Application No. PCT/EP2007/006279 filed on Jul. 16, 2007, which claims priority from German Patent Application No. DE 10 2006 034 905.9 filed on Jul. 28, 2006, the disclosure of which is incorporated herein by reference in its entirety.

BACKGROUND OF THE INVENTION

1. Field of the Invention

Short-pulse lasers are used for time-resolved measurement of fluorescence phenomena (energy transfer, FLIM).

The fluorophore is excited by a strong ultrashort laser pulse and the decay in fluorescence over time is analyzed.

2. Description of Related Art

It is known from DE 10033180A1, which makes up part of the present disclosure, to spectrally resolve the fluorescence signal coming from the sample and to record the spectral components with a multichannel detector. In acquiring FLIM information from a multichannel detector, for example, a 32-channel PMT by Hamamatsu, it is important to record the incoming signals simultaneously, accurately with respect to time, and without dead times in the simplest possible manner.

SUMMARY OF THE INVENTION

The present invention offers a particularly advantageous approach to this problem.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
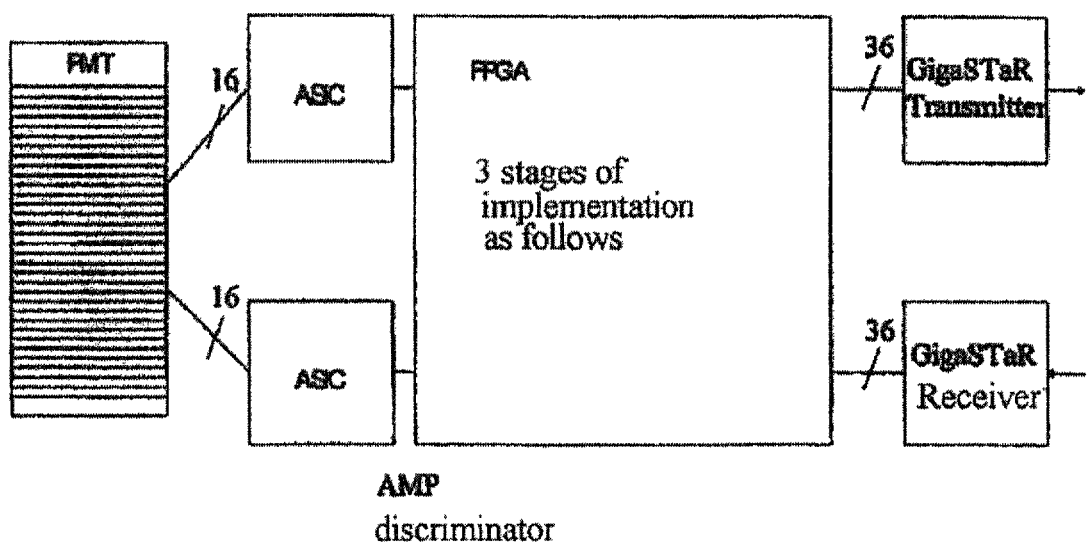
FIG. 1 shows a 32-channel PMT according to DE 10008594 A1 which supplies time-dependent intensity and spectrum data.

FIG. 1 shows a 32-channel photo multiplier tube ("PMT") according to DE 10008594 A1 which supplies time-dependent intensity and spectrum data. The PMT is followed by two application specific integrated circuits ("ASICs") (e.g., by Hamamatsu), each operating 16 channels in photon counting mode.

Figure 2:
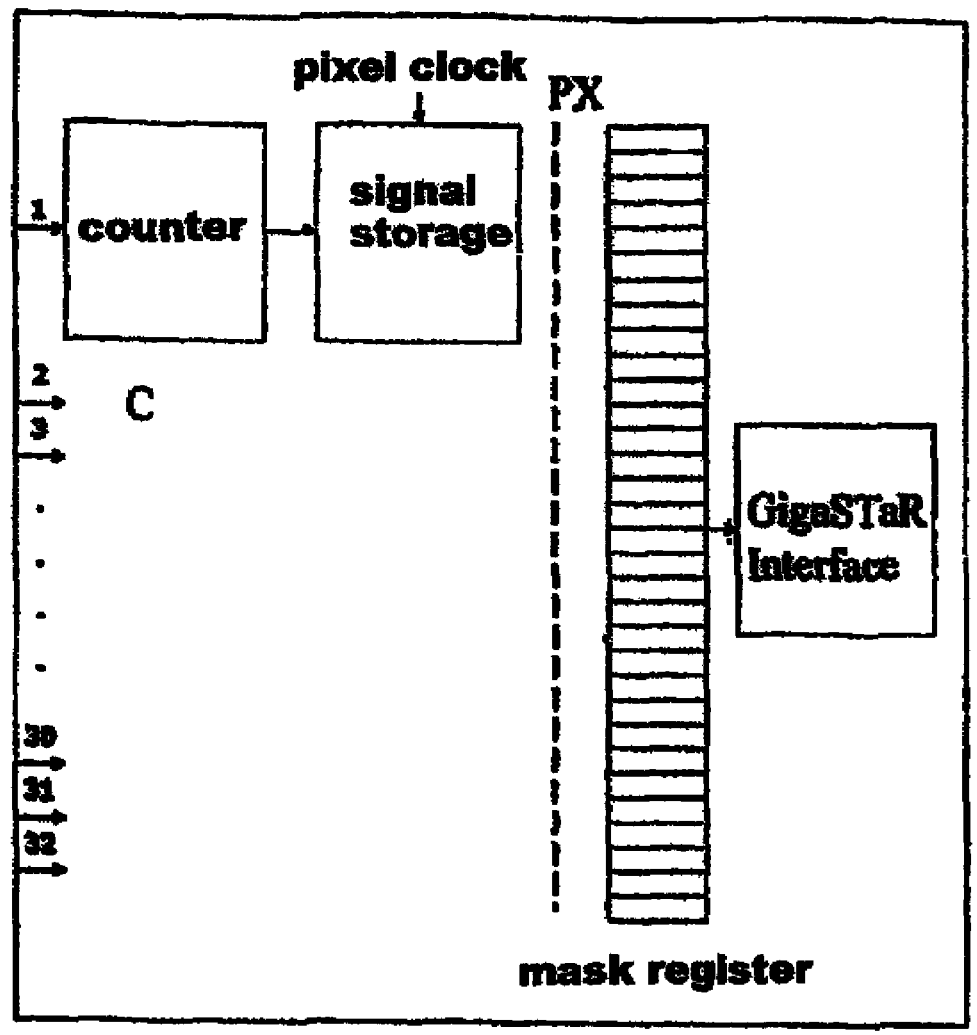
FIG. 2 shows the first step of an FPGA determining the number of pulses arriving per channel within a counting period determined by a pixel clock and their distribution over time according to an embodiment of the present invention.

Switching thresholds are determined by comparators for noise cancellation, and a pair of differential leads is provided at the output of the ASICs for each PMT channel to prepare digital 1 or 0 data (pulse or no pulse). The number of pulses arriving per channel within a counting period determined by a pixel clock and their distribution over time is now determined. This is carried out, according to the invention, in an FPGA (free programmable gate array). The first step is shown in FIG. 2. An asynchronous counter C into which all of the pulses enter is associated with each PMT channel in the FPGA. The pulses per time unit are stored in registers by a counter. Every counting time has a register and the counting time can be stored in memory by this register. This is carried out by means of drawers, as it were (32 gates in the register), and only pertinent data are stored.

The system-spanning pixel clock PX determines the time at which the actual counter state is temporarily stored and prepared for transfer to memory (PC) via interface (Giga Star).

After the counters are read out they are erased and the counting process restarts.

Figure 3A:
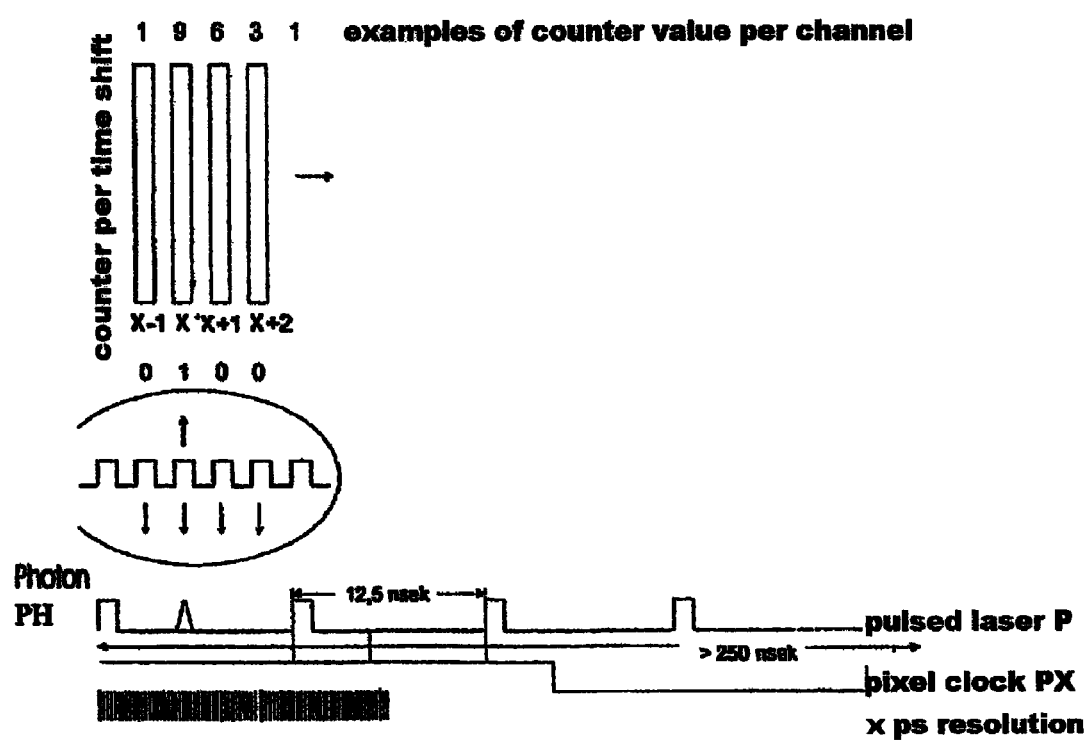
FIG. 3a is a schematic depiction of the timing of the pixel clock PY according to an embodiment of the present invention.

FIG. 3a is a schematic depiction of the timing of the pixel clock PY which represents a laser pulse P triggering a sample reaction and the incoming photons as sample reaction per PMT channel.

Time windows X, X+1, etc. within a counting cycle (time between two laser pulses) is shown in the top portion. Counting registers are provided for the individual time windows.

Figure 3B:
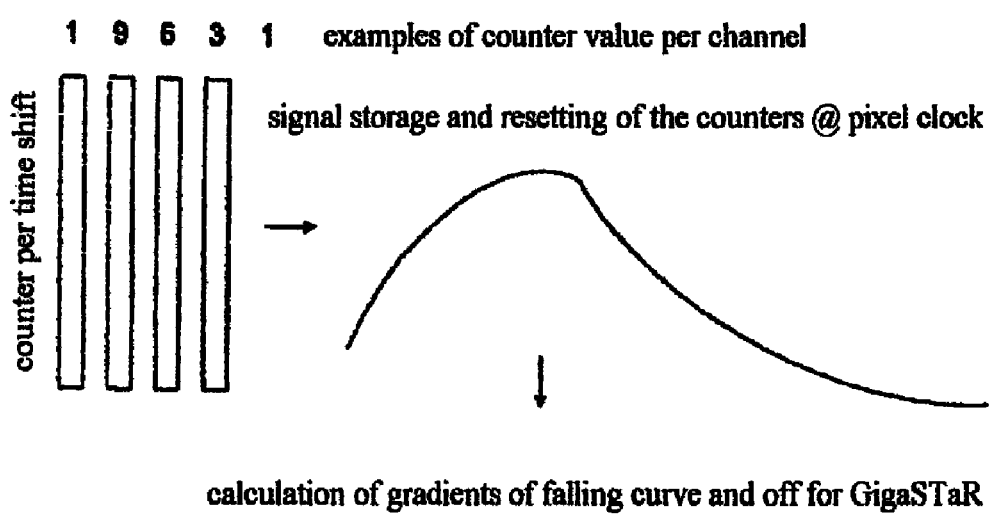
FIG. 3b shows the signal shape over time per PMT channel according to an embodiment of the present invention.

FIG. 3b shows the signal shape over time per PMT channel that would correspond to the readout of the counting register. For example, the entire spectral region is not taken into consideration.

Figure 4:
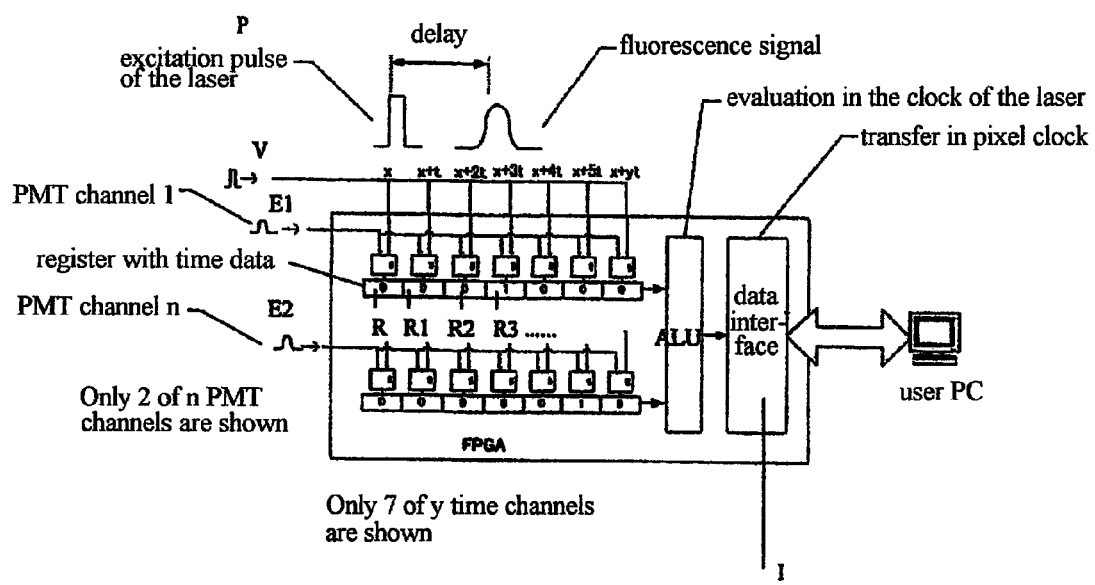
FIG. 4 shows how the time evaluation is carried out within the FPGA according to an embodiment of the present invention.

FIG. 4 shows how the time evaluation is carried out within the FPGA. For example, the inputs E1, E2 coming from two PMT channels which receive the digitized signals of the ASICs are shown.

Hardware wiring V of different length or programmable delay channels (shown) ensure that registers R, R1, R2 are each opened at different times X, x+1, X+2t and, therefore, the pulses entering via the inputs E1, E2 reach the register which is uniquely associated with a time which corresponds to a determined delay after a start signal is triggered (excitation pulse P of the laser). With respect to hardware, 64 inputs, for example (bit length for a data board) are taken and the pins are connected to one another from the outside by a lead V of determined length. Only the register with the arriving pulse(s) has a signal 1; the others have 0. The time data are now available.

The values are transferred to registers as counting values per channel.

The registers R with the time data contained therein are read out in the timing of the excitation pulses P and the data are transferred to storage and evaluation media (PC) via an interface.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. An arrangement for processing signals at an output of a multichannel detector in a spectrally resolved acquisition of time-variable fluorescence phenomena in a microscope; wherein an FPGA (free programmable gate array) is arranged downstream of the output of the multichannel detector; and wherein a time correlation of incoming measurement values is carried out in the FPGA, by at least one of hardware wiring of different lengths and programmable delay, by opening different registers at different times.

2. The arrangement according to claim 1;
   wherein asynchronous counters are associated with PMT channels in the FPGA.

3. The arrangement according to claim 1;
   wherein a time clock preset (pixel clock) is provided which determines when a counter state is read out and stored.

4. The arrangement according to claim 3;
   wherein laser pulses which trigger sample reactions are correlated in time with the pixel clock.

5. Laser scanning microscope according to claim 1 further comprising a dispersion means for spectral resolution of fluorescent light and a multichannel detector for acquiring the spectral components in a plurality of spectral channels.

* * * * *